United States Patent [19]
Kim et al.

[11] Patent Number: 5,166,378
[45] Date of Patent: Nov. 24, 1992

[54] SELECTIVE MONOACYLATION OF SUBSTITUTED HYDRAZINES

[75] Inventors: Chang K. Kim, Pittsford; Francesco Debellis, Rochester; Michael E. Campbell, Kendall, all of N.Y.

[73] Assignee: Eastman Kodak Company, Rochester, N.Y.

[21] Appl. No.: 527,981

[22] Filed: May 24, 1990

[51] Int. Cl.$^5$ .................. C07C 243/28; C07C 243/38; C07C 317/32
[52] U.S. Cl. .............................. 554/54; 544/8; 544/10; 564/148; 564/149; 564/150; 564/151
[58] Field of Search .............. 544/8, 10; 260/401, 260/404.5; 564/148, 149, 150.151; 554/54

[56] References Cited

U.S. PATENT DOCUMENTS 4,803,277  2/1989  Shiokawa et al. .................. 514/332

FOREIGN PATENT DOCUMENTS 1098002  1/1961  Fed. Rep. of Germany .
2134482  1/1972  Fed. Rep. of Germany .
883379  11/1961  United Kingdom .
2087868  6/1982  United Kingdom .

OTHER PUBLICATIONS

Synthesis, Nov. 1990, R. S. Hosmane et al, "Synthesis of a Novel Ring-Expanded Xanthine Analogue and Several Methyl or Benzyl Derivatives Containing the 5:7--Fused Imidazo [4,5-e][1,2,4] Triazepine Ring System" pp. 1095–1100.

*Primary Examiner*—Richard L. Raymond
*Attorney, Agent, or Firm*—Robert A. Gerlach

[57] ABSTRACT

Mono-acylated hydrazines are prepared in high yield by reaction of a hydrazine salt with an azole derivative of acyl halide in the presence of a strong base. Useful hydrazine salts include those of the formula $RNHNH_2 \cdot HX$, where R is alkyl, aryl, aralkyl, acyl, aroyl, heterocyclic or heteroaryl, and HX is a mineral or organic acid. Useful azole derivatives include those of the formula R'CO—A, where R' is alkyl, aryl, aralkyl, heterocyclic or heteroaryl and A is an azole radical such as pyrrole, imidazole, pyrazole, triazole, tetrazole, indole or benzimidazole.

9 Claims, No Drawings

SELECTIVE MONOACYLATION OF SUBSTITUTED HYDRAZINES

FIELD OF THE INVENTION

This invention relates to the formation of monoacylated substituted hydrazines. More particularly, it relates to the preparation of such compounds via use of acyl azoles as acylating agents.

Acyl halides are well known acylating agents. They have been used to prepare a wide variety of acyl derivatives. For these reasons the present inventors examined the utility of such agents in the formation of certain acyl compounds useful in the photographic arts. Thus, in their work, the present inventors investigated the use of acyl halides in reactions illustrated by the following equation:

$$RNHNH_2 \cdot HX + R'COCl \longrightarrow RNHNHCOR' + NEt_3 \cdot HCl \quad (1)$$
$$\quad\quad 2 \quad\quad\quad 3 \quad\quad\quad\quad 1$$

Results indicated that such processes were not satisfactory for the inventors' purposes. It was found that the reactions were usually too rapid, exothermic, and difficult to adequately control. Moreover, it was found that, in addition to the desired monoacylated derivative, other undesired mono-, di- and triacylated co-products, were formed in varying amounts. Furthermore, it was found that even small amounts of the polyacylated co-products had profound adverse effects. For example, their presence made it difficult to isolate the desired monoacylated product from the reaction mixture in co-products adversely interfered in reactions in which the monoacylated products were used as chemical intermediates.

Faced with these problems, the present investigators had to devise a new method for formation of acylated products. The new method, described in detail below, is straight forward, readily carried out, and readily adaptable to use in industry. Accordingly, it is believed that the present invention is a significant advance in the art.

SUMMARY OF THE INVENTION

It has been discovered that the problems with acyl halides noted above can be overcome by use of a new type of acylating agent. More specifically, this invention comprises the use of acyl azoles as selective acylating agents. Thus, they can be used when it is desirable to form a monoacylated product from a compound which is susceptible to polyacylation. In a particular aspect, this invention provides means for manufacturing substituted acyl hydrazines $$RNHNHCOR' \quad\quad (I)$$

wherein R and R' are alike or different. In a preferred embodiment, R' is a bulky organic substituent.

The acyl azoles used in this invention are readily prepared by reacting a one mole portion of an acyl halide with two mole portions of an azole. The azole can be selected from a wide variety of H azoles, such as those set forth below in this specification.

As part of the invention, it has also been discovered that the acyl azoles need not be employed in pure form. Stated more particularly, they can be employed in the reaction mixtures in which they are produced; preferably after removal, e.g. by filtration, of the azole acid salt formed as a by product.

In the first equation which follows, preparation of an acylating agent of this invention is illustrated. The second equation illustrates the process of this invention.

This process is independent of the method employed for formation of the acyl azole. However, a preferred embodiment, the acyl azole is employed in the reaction mixture in which it is produced (preferably after removal of A—H·HCl or equivalent azole-acid salt). To illustrate this embodiment the acyl azole (R'CO—A) is enclosed in brackets in both equations in order to signify that the acyl azole product of the first equation is used in the process of the second.

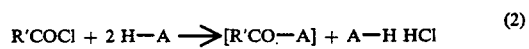

$$R'COCl + 2 H-A \longrightarrow [R'CO-A] + A-H\;HCl \quad (2)$$
$$\quad 3 \quad\quad\quad\quad\quad\quad\quad 5$$

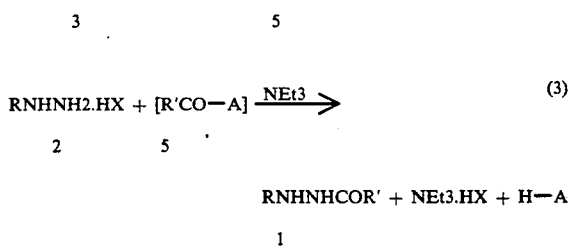

$$RNHNH_2 \cdot HX + [R'CO-A] \xrightarrow{NEt_3} \quad (3)$$
$$\quad 2 \quad\quad\quad\quad 5$$

$$RNHNHCOR' + NEt_3 \cdot HX + H-A$$
$$\quad\quad 1$$

As part of this invention, it has also been discovered that when acyl azoles are reacted with substituted hydrazines 2, the process can be conveniently carried out. Stated another way, the reaction proceeds at a rate which can be readily controlled. Furthermore, the process is not overly exothermic; hence any heat generated does not require burdensome means for control of selected, low reaction temperatures. Moreover, the reaction is much more selective for the information of the desired monoacyl derivates 1; only minimal amounts of di- and triacylated products are produced.

The utility of the invention can be illustrated as follows:

In the synthesis of a photographically useful monoacylhydrazine 1a, the acylation reaction of an aryl hydrazine hydrochloride 2a with a large acyl chloride 3a in the presence of tributylamine

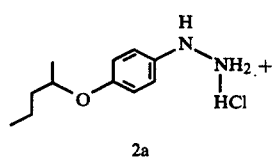

2a

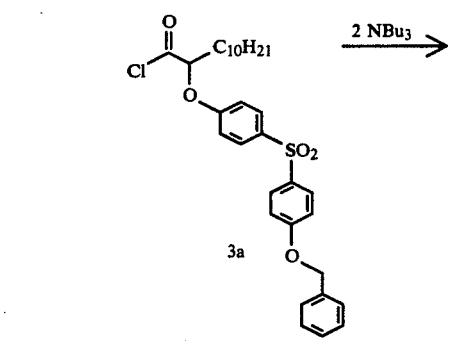

3a

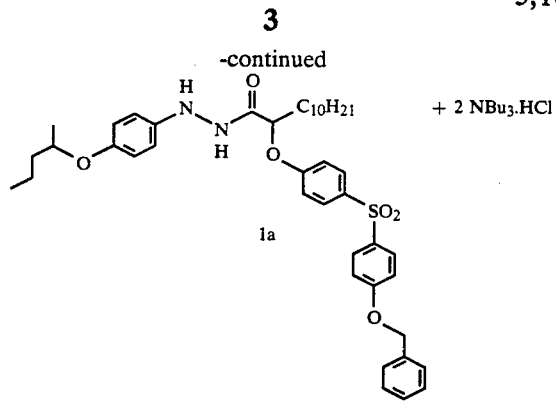

(i) generates multi acylated by products in varying amounts which interfere with the crystallization of the desired product 1a and (ii) gives disappointing results in the rate of crystallization and the yield. The best yield of 1a in this reaction is 35–40%.

In contrast, when the aryl hydrazine hydrochloride 2a is reacted with the acyl imidazole 5iia (see Example 1 below) the desired acylhydrazine 1a is obtained in 76% yield.

As another example of this invention, the monoacylhydrazine 1b is useful as an intermediate in the synthesis of photographic chemicals. It can be produced by reaction of a heterocyclic hydrazine hydrochloride 2b and large acyl chloride 3b as illustrated by the following equation wherein NEt$_3$ is triethylamine.

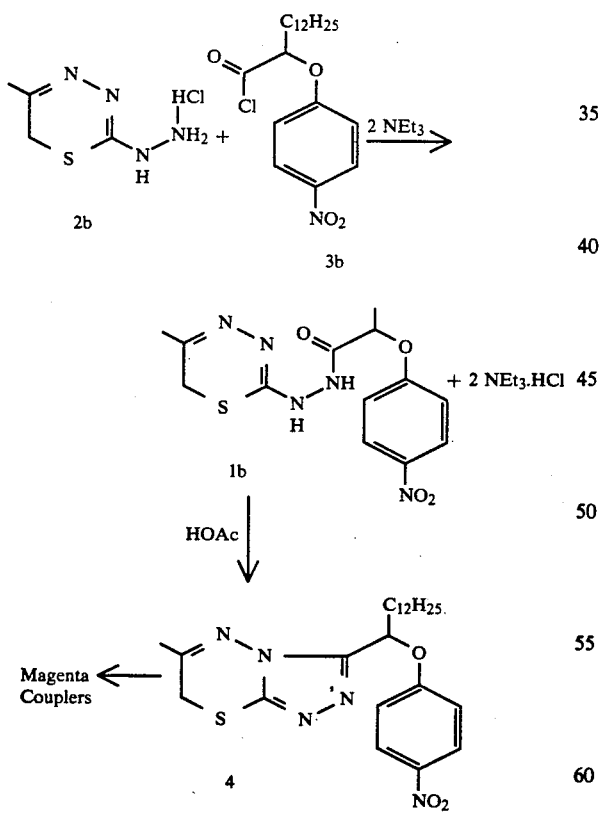

The above reaction also produces multi acylated by products which affect the isolation of the desired product 1b. Without isolation and purification of 1b, the impurities are carried on to the subsequent steps and transformed to new impurities which are difficult to remove. The best yield of isolated 1b from this reaction without any significant amounts of impurities is 45–50%.

In contrast, when the process of Example 2 (below is used, reaction of the substituted hydrazine 2b with imidazole derivative 5iib gives the acylhydrazine 1b so cleanly, that the next ring closure step to give 4 can be carried out without isolation of the acylhydrazine 1b. The overall yield of the ring closed product 4 is 80–85% which compares to the overall yield of 35–45% when the acylhydrazine 1b is made using the acyl chloride 3b, isolated, and used in the next ring closure step. If the acyl hydrazine 1b needs to be isolated, it can easily be done in 85–90% yield. However, the non isolation process is desirable since it saves solvent, labor, and process time substantially. The throughput and manufacturing cost are dramatically improved for the ring closed product 4.

DESCRIPTION OF PREFERRED EMBODIMENTS

In a preferred embodiment, this invention provides a method for the monoacrylation of monosubstituted hydrazine salts, R—NH—NH$_2$·HX, wherein R is an inert organic group and X is an inert anion, said method comprising reacting said salt with an acyl azole

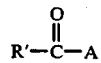

A is a group derived from a 1H azole; said process being carried out in the presence of a strong base to combine with by product protic acid.

In another preferred embodiment, the process comprises two steps; formation of the acyl azole from a 1H azole and an acyl halide, and use of the acyl azole thereby produced in the process comprising the embodiment set forth above.

For the purpose of this invention, an "azole" (signified by "A" herein) is defined as a 5-membered heterocyclic ring containing at least one nitrogen having a hydrogen bonded thereto, and having two conjugated double bonds. As shown by the following examples, the rings may be isolated as in pyrrole, or in a fused ring system such as benzimidazole. As can be seen, when there are two or more nitrogens in the ring, they may be adjacent or separated from one another. In the following examples of azoles for use in this invention, the above mentioned hydrogen atom bonded to the nitrogen atom is attached to the unsatisfied valence line depicted in the examples. When the azoles are transformed into acyl azoles for use in this invention, the acyl group is bonded to the valence line shown.

| Examples of Azoles | |
|---|---|
| (i) | 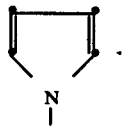 pyrrole, |

-continued

Examples of Azoles (ii) 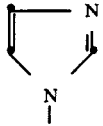 imidazole, (iii) 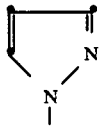 pyrazole, (iv) 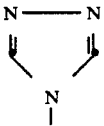 triazole, (v) 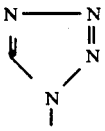 tetrazole, (vi) 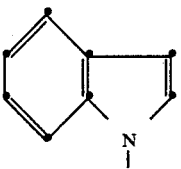 indole, (vii) 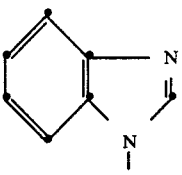 benzimidazole.

As can be seen from the above examples, preferred azoles have only one nitrogen atom bonded to hydrogen. Although the azole may have substituent groups other than hydrogen bonded to one or more atoms in the ring, for this invention it is preferred that the acyl group be the only substituent. It is also preferred that only one acyl group be present. The azole may have more than two rings; for example there may be three rings in a fused ring system. When three or more rings are present, it is preferred that they also have the structural characteristics discussed above for the one and two ring azoles.

As can be seen by Equation (3), in a preferred aspect this invention is directed to processes in which the azole group does not appear in the desired acylated product. Accordingly, a skilled practitioner will consider use of simple, less expensive, readily available azoles for use in the processes of this invention. Such compounds are within the preferred types of azoles discussed above. Of those types, it is preferred to use an azole with only one ring. Of these classes of useful azoles, acyl imidazoles are preferred.

Preparation of Acyl Azole

As shown by Equation (2), acyl azoles for use in this invention are conveniently prepared by reacting a 1H azole with an acyl halide such as

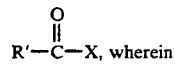 wherein

X is preferably chlorine or bromine. To facilitate this reaction, it is preferred that the azole not have any substituents which will compete for reaction with the active halogen in the acyl halide. Stated another way, it is preferred that the hydrogen bonded to the nitrogen in the azole, be the only active hydrogen in the azole which is capable of reacting with the acyl halide at the temperature (and other reaction conditions employed to form the acyl azole $R'$—CO—A.

Above it was mentioned that an acyl halide

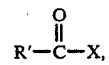

can be used to prepare an acyl azole. A skilled practitioner will recognize that the acyl halide employed for this purpose may be replaced with the corresponding carboxylic acid or anhydride.

As illustrated by Equation (2), acyl azoles for use in this invention are conveniently prepared by reacting two moles of azole with one mole of acyl halide. It is not necessary that the azole be contacted in this ratio, and an excess of azole can be used if desired.

The acyl halide and azole are conveniently reacted at ambient pressure, although greater or lesser pressures can be used. Preferably they are reacted at a temperature of $-10°$ C. to about 50° C. Temperatures somewhat outside this range can be reaction temperature (like the pressure) is not critical, and any temperature that gives a convenient rate of reaction and does not cause an undue amount of decomposition or side reaction can be employed.

The reaction time is not a truly independent variable and is dependent at least to some extent on the other reaction conditions employed and the inherent reactivity of the reactants. In general, higher temperatures afford shorter reaction times. In general reaction times from one minute to six hours are sufficient.

The preparation of acyl azoles is conveniently carried out in an inert organic solvent. Preferably, the solvent selected is one in which by-product azole acid salt is insoluble so that this material can be conveniently removed by filtration prior to the reaction illustrated by Equation (3). Esters, nitriles, hydrocarbons, halogenated hydrocarbons, and the like are examples of suitable solvents. The solvent may be used in the process of Equation (3). Stated another way, in a preferred embodiment, the solvent for the reaction of Equation (2) is not removed from the acyl azole before conducting the process of Equation (3).

As already discussed, 1H-azoles of the type discussed above readily react with acyl halides such as acyl chlorides and acyl bromides. Hence, a wide variety of acyl azoles are available for use in this invention. Furthermore, the nature of the group $R'$ in the acyl azoles:

is not critical for the process of this invention, hence, a wide variety of R' groups may be present in the acyl azoles employed in the process of this invention for making monoacylated monosubstituted hydrazines.

For this invention it is only necessary that the substituent R' be an "inert substituent". An "inert substituent" or "inert organic group" has the following characteristics:

(1) It is stable, or substantially stable, under the reaction conditions employed in the process of this invention: i.e. it does not decompose to an untoward extent during reaction(s) employed in this invention.

(2) It is non reactive, or substantially non reactive toward the other reagents used in the process of this invention; i e. it does not undergo an extraneous side reaction (to an unacceptable extent) with the other ingredient(s) used in the process of this invention.

(3) It does not prevent, by steric hindrance or other mechanism or effect, the formation of the product desired.

Thus R' may be, for example, alkyl, aryl, heterocyclic or heteroaryl. The number of carbon atoms in R' is not critical. Stated another way, the process of this invention is not dependent on the number of carbon atoms in R'. for convenience, the number of carbon atoms in R' is usually from about one to about 30 carbon atoms; however, a greater number of carbon atoms can be present. The R' substituent need not be solely composed of carbon or hydrogen. Instead it may have other groups which are inert toward the hydrazine reactant e.g. nitro, carboxy, nitrile, alkoxy, aryloxy, blocked amine, etc.

Although the radical R' in the acyl azole may be selected from simple substituent groups, in a preferred embodiment R' is a bulky substituent. Bulky substituents are illustrated by the groups attached to the imidazole rings in reactants 5iia and 5iib in Examples 1 and 2, respectively. As an be seen such groups have alkyl groups higher than C8 and at least one benzene ring. Thus, for the purpose of this invention, "bulky" signifies an inert organic substituent having from about 8 to about 30 or more carbon atoms.

To prepare the monoacylated hydrazine

RNHNHCOR'     (I)

according to the process of this invention, an acyl azole, such as described above, is reacted with a monosubstituted hydrazine salt RNHNH2·HX, wherein R is alkyl, aryl, aralkyl, acyl, aroyl, heterocyclic or heteroaroyl and the like, and HX is a mineral or organic acid. As can be seen, the nature of R is not critical. Accordingly, it can be selected from a wide variety of "inert organic groups" or "inert substituents" as defined above. Again R, may have from one to about 30 or more carbon atoms and may have substituents such as —NO2, —NRR, COOR, —CN, etc.

R and R' may be alike or different. They are selected in order to form the product desired. In a preferred embodiment of this invention, they are selected in order to yield compounds of interest in the photographic arts. Thus, they are selected to yield compounds that have use in photographic chemistry, or to yield compounds which can be used as intermediates for preparing compounds having photographic utility.

Although the process of this invention can be conducted using a hydrazine, RNHNH2, it is preferred that the acyl azole be reacted with a hydrazine salt, RNHNH2·HX wherein HX is a mineral or organic acid. Such salts are more readily handled than the free hydrazine.

In the salts, the nature of HX is not critical. However, since it is not incorporated in the final product, it is preferred that a non-expensive acid salt be used. It is also preferred that the acid be inert so that it does not enter into an unwanted side reaction with one or more of the other ingredients present in the reaction mixture. Hence, it is preferred that HX be a lower carboxylic acid, e.g. acetic acid or the like, or more preferably a mineral acid. Preferably X is Cl— or Br—, but it may also be another inert anion such as SO4= or HSO4—.

In the process of this invention, one mole of acyl azole

reacts with one mole of mono substituted hydrazine or a salt thereof, R—NHNH2·HX. It is not necessary that the reactants be contacted in this ratio, and an excess of either reactant can be used. Although there is no limit on the amount of excess that can be employed, it is preferred to use molar equivalent (stoichiometric) or substantially stoichiometric amounts in order to simplify the process and product work up. Thus, it is preferred that the relative amounts of reactants be stoichiometric ±0.5 mole %.

The reactants are contacted in the presence of a base to combine with by-product HX. The nature of the base is not critical. Inorganic or organic bases may be used. Preferably the base is a tertiary amine. Preferred tertiary amines are tri (lower alkyl) amines, wherein the alkyl groups have two to about five carbon atoms. The base is preferably used in a quantity to react with all acid formed as a by product. In general stoichiometric quantities and or stoichiometric plus an excess of about 0.1 mole percent is used.

The reactants and base are contacted in an organic solvent of the type mentioned above.

The reaction of the acyl azole and monosubstituted hydrazine is preferably carried out at ambient pressure. Higher and lower pressures can be used. The process is conducted at a temperature which gives a reasonable rate of reaction without an temperatures of 10° C. to about 40° C. are used; however, temperatures somewhat outside this range can be employed.

The reaction time is not a truly independent variable but is dependent at least to some extent on the other reaction conditions employed. Generally, higher reaction temperatures afford shorter reaction times. Generally, reaction times of 0.5 hour to 5.0 hours are used.

The following examples serve to illustrate the process of this invention.

EXAMPLE 1

2-(2-[4-{(4-[Phenylmethoxy]phenyl)sulfonyl}phenoxy]dodecanoyl)-1-(4-[1-methylbutoxy]phenyl)-hydrazine (1a)

(i) comparative example with acyl chloride 3a

A mixture of 13.85 g (0.06 m) of 4-(1 methylbutoxy)-phenylhydrazine hydrochloride (2a) and 22.2 g (0.12 m) of tributylamine in 70 ml of ethyl acetate is cooled to 0° C. under nitrogen. A solution of 33.4 g (0.06 m) of 2-(4-[{4-(phenylmethoxy)phenyl}sulfonyl]phenoxy)dodecanoyl chloride (3a) in 160 ml of ethyl acetate is added slowly to the mixture keeping the temperature at 0-5° over an hour. The resulting mixture is stirred at 0-5° C. for 30 min, warmed up to room temperature, and stirred at that temperature for another hour. To the mixture is added 100 ml of water with vigorous stirring. After the layers separate, the lower water layer is washed with dilute hydrochloric acid and then water, dried over magnesium sulfate, and concentrated to a red brown oil. The oil is crystallized from isopropyl ether to give a crude product which is then recrystallized from methanol. The product obtained is 18.0 g (42%) with 85 area % by HPLC.

(ii) Process of this invention with imidazole derivative 5iia

To a solution of 33.4 g (0.06 m) of 2-(4-[{4-(phenylmethoxy)phenyl}sulfonyl]phenoxy)dodecanoyl chloride (3a) in 160 ml of ethyl acetate is added 8.2 g (0.12 m) of imidazole. The mixture is stirred at room temperature for an hour and filtered to remove the precipitated imidazole hydrochloride. The filtrate containing 1-(2-[4-{(4-[phenylmethoxy]phenyl)sulfonyl}phenoxy]-dodecanoyl)-1H-imidazole (5iia) is added to a mixture of 13.85 g (0.06 m) of 4-(1-methylbutoxy)phenylhydrazine hydrochloride (2a) and 11.1 g (0.06 m) of tributylamine in 70 ml of ethyl acetate at room temperature. The mixture is stirred for 2 hours and worked up in the same manner as in (i) above. The resulting red brown oil is crystallized from 450 ml of isopropyl ether to give 32.6 g (76%) with 92 area % by HPLC.

EXAMPLE 2

6-Methyl-3-(1-[4-nitrophenoxy]tridecyl)-7H-1,2,4-triazolo(3,4-b)-1,3,4-thiadiazine (4) via 2-(2-[nitrophenoxy]tetradecanoyl)-1-(5-methyl-6H-1,3,4-thiadiazin 2-yl)hydrazine (1b)

(i) Comparison with acyl chloride 3b

A mixture of 24.25 g (0.134 m) of (5-methyl-6H-1,3,4-thiadiazin-2-yl)-hydrazine hydrochloride (2b) and 25.9 g (0.256 m) of triethylamine in 170 ml of acetonitrile is cooled to 0° C. A solution of 46.8 g (0.122 m) of 2-(4-nitrophenoxy)tetradecanoyl chloride (3b) in 50 ml of ethyl acetate is added slowly to the mixture keeping the temperature at 0-5° C. over an hour. The resulting mixture is stirred at 0° C. for 30 min, then warmed up to room temperature and stirred for another hour. After the reaction is complete, 170 ml of ethyl acetate is added and the mixture is stirred for 15 min. The solid is collected, washed with ethyl acetate, dried, and reslurried in 300 ml of water to remove triethylamine hydrochloride. The product is collected, washed with water, and dried to give 33.0 g (55%) of 2-(2-[4-nitrophenoxy]tetradecanoyl)-1-(5-methyl 6H-1, 3,4 thiadiazin-2-yl)hydrazine (1b) with 93 area % by HPLC.

A solution of 33.0 g of the above substituted acylhydrazine 1b in 132 ml of acetic acid is heated with stirring at 95° C. for 2 hours. At the end of the reaction, 65 ml of isopropyl alcohol is added to the reaction mixture. And then the whole mixture is added with stirring to 200 ml of 70° C. water. After cooling to 20° C. and stirring at that temperature for an hour, the product is collected, washed with water, dried, and recrystallized from isopropyl alcohol to give 27.2 g (47% overall from 3b or 86% from 1b) of 6-methyl3-(1-[4-nitrophenoxy]-tridecyl)-7H-1, 2,4 triazolo(3,4-b)-1,3,4 -thiadiazine (4) with 95 area % by HPLC.

(ii) Process of this invention with imidazole derivative 5iib

To a solution of 46.8 g (0.122 m) of 2-(4-nitrophenoxy)tetradecanoyl chloride (3b) in 225 ml of ethyl acetate is added 16.6 g (0.244 m) of imidazole. The mixture is stirred at room temperature for 30 min and filtered to remove the precipitated imidazole hydrochloride. The filtrate containing 1-(2-[4-nitrophenoxy]tetradecanoyl)-1H -imidazole (5iib) is added to a mixture of 22.0 g (0.122 m) of (5-methyl-6H-1,3,4-thiadiazin-2-yl)-hydrazine hydrochloride (2b) and 12.3 g (0.122 m) of triethylamine in 200 ml of ethyl acetate. The mixture is stirred at room temperature for an hour. At this point, if it is necessary, the acylhydrazine 1b can be isolated by collecting the solid, washing with ethyl acetate, drying, reslurrying in water, collecting and drying to give 54.0 g (90%) with 98 area % by HPLC. However, the reaction mixture can be used directly in the next ring closure step without isolation of the substituted acylhydrazine 1b. Thus, at the end of reaction, 45 ml of acetic acid is added to the reaction mixture, and the mixture is heated under reflux (approximately 80° C.) for an hour, after which the ring closure reaction is complete. To the reaction mixture is added 400 ml of water and the mixture is stirred at 60° C. for 15 min. After the layers settle, the lower water layer is discarded and the upper ethyl acetate solution is concentrated under reduced pressure to about 40% of the original volume. The resulting mixture is cooled to 20° C. and stirred at that temperature for 30 min. The solid is collected, washed with heptane, and dried to give 48.5 g (84% overall from 2b or 3b) of 6-methyl-3-(1-[4-nitrophenoxy]tridecyl)- 7H-1,2,4-triazolo-(3,4-b)-1,3,4-thiadiazine (4) with 99 area % by HPLC.

In the following examples all parts are by weight.

EXAMPLE 3

Preparation of 2-(2-[4-{(4-[Phenylmethoxy]phenyl)-sulfonyl}-phenoxy]dodecanoyl)-1-(4-[1-methylbutoxy]-phenyl) hydrazine (1a)

2-(4-[{4-(phenylmethoxy)phenyl}sulfonyl]phenoxy)-dodecanoic acid, 81.75 parts, is suspended in 370 parts of ethylacetate, and reacted with 38.5 parts of oxalyl chloride in the presence of 0.075 parts of N,N dimethyl-formamide at 30° C. for 30 minutes and then refluxed for one hour. The resultant acid chloride is then reacted with 20.75 parts of imidazole at 20° C. for 90 minutes, and the resultant mixture filtered. The filtrate is then reacted at 25° C. with 38.5 parts of 4-(1 methylbutoxy)-phenylhydrazine monohydrochloride in the presence of 30.8 parts of tributylamine for two hours.

Thereafter, the resultant reaction mixture is washed twice with 2.9 parts of conc. hydrochloric acid in 250 parts of water and then with 250 parts of H₂O.

After separation of the water, the ethyl acetate is removed by codistillation with methanol (5×200 part portions of methanol being added and the codistillation conducted at 65° C. under vacuum. The product oil is dissolved in 542 parts of methanol.

The methanol/product solution is cooled slowly to 10° C. with tempered water and stirred 12-16 hours to crystallize product. After crystallization 100-200 parts of methanol is added to thin the slurry, and the product crystals collected on a filter press. The methanol damp product is air dried at 40° C. to a volatiles loss of ≦1.0%.

The 100.8 part yield is 92.9% of theory.

EXAMPLE 4

Preparation of 6-Methyl-3-1(1-[4-nitrophenoxy]tridecyl)-7H-1,2,4-tritr iazolo[3,4-b][1,3,4]thiadiazine (4)

A glass lined reactor is charged with 589 parts of ethyl acetate and 129 parts of 2-(4-nitrophenoxy)tetradecanoyl chloride (3b). While the mixture is stirred, 46 parts of imidazole is added keeping the temperature between 20-25° C. over a 10-15 minute period. The reaction mixture is stirred at room temperature for 30 minutes and filtered through a filter press to collect imidazole hydrochloride. The filtrate is added to the stirred mixture of 61 parts of (5-methyl-6H-1,3,4-thiadiazin-2-yl)-hydrazine hydrochloride (2b) and 34 parts of triethylamine in 510 parts of ethyl acetate in another vessel. The mixture is stirred at room temperature for 1 hour.

To this reaction mixture is added 130 parts of acetic acid and the mixture is heated under reflux for 1 hour. After the 1 hour reflux period 1090 parts of hot tap water are added. The mixture is stirred for 15-20 minutes and allowed layers to separate. The colorless bottom layer is separated and the upper organic layer is concentrated to approximately half volume under reduced pressure. The mixture is then cooled to 20° C. and kept at that temperature for 2 hours. The product is collected in a filter box and dried in a 45° C. rotary drier to a volatiles loss of ≦1.0%. The product yield is 119 parts or 75% of theory.

We claim:

1. A process for the preparation of a mono-acylated substituted hydrazine RNHNHCOR', said process comprising:

(a) reacting R'COCl with 2 mole equivalents of HA to produce an acyl azole,

(b) subsequently removing azole acid salt A·H·HCl by-product, and (c) reacting a monosubstituted hydrazine salt R-NH-HNH$_2$·HX with said acyl azole

wherein R is an alkyl, aryl, aralkyl, or acyl group of up to about 30 carbon atoms,
   R$^1$ is an alkyl or aryl group having from about 8 to about 30 carbon atoms,
   and A is an azole group;
   said process being further characterized by forming said monacylated hydrazine RNHNHCOR' with less other mono-, di- and tri-acylated co-product than when said acyl azole is reacted with $$R'-\overset{O}{\underset{\|}{C}}-Cl$$

2. The process of claim 1 wherein A is a pyrolle, imidazole, pyrazole, triazole, tetrazole, indole or benzimidazole group.

3. Process of claim 1 conducted in an inert solvent.

4. Process of claim 1 conducted at a temperature of from about −10° C. to about 40° C.

5. The process of claim 1 wherein step (c) is conducted in the presence of a strong base.

6. Process of claim 5 wherein aid strong base is a tertiary (lower alkyl) amine.

7. The process of claim 2 wherein said azole is imidazole.

8. Process for the preparation of 2-2(2[4-{4-[phenylmethoxy]phenyl)sulfonyl}-phenoxy]dodecanoyl)-1-(4-[1-methylbutoxy]phenyl)-hydrazine, said process comprising reacting 1-(2-[4-{(4-[phenylmethoxy]phenyl)sulfonyl}phenoxyl]-dodecanoyl)-1H-imidazole with 4-(1-methylbutoxy)phenylhydrazine hydrochloride.

9. The process of claim 8 further characterized by being conducted in the presence of tributylamine and in ethyl acetate solvent.

* * * * *